US009377300B2

(12) United States Patent
Moreau et al.

(10) Patent No.: US 9,377,300 B2
(45) Date of Patent: Jun. 28, 2016

(54) PHOTOREFLECTANCE DEVICE

(71) Applicants: NEXCIS, Rousset (FR); UNIVERSITE D'AIX MARSEILLE, Marseilles (FR)

(72) Inventors: Antonin Moreau, Rousset (FR); Véronica Bermudez, Rousset (FR); Ludovic Escoubas, Marseilles (FR); Jean-Jacques Simon, Peypin (FR)

(73) Assignees: NEXCIS, Rousset (FR); UNIVERSITE D'AIX-MARSEILLE, Marseilles (FR)

( * ) Notice: Subject to any disclaimer, the term of this patent is extended or adjusted under 35 U.S.C. 154(b) by 0 days.

(21) Appl. No.: 14/651,414

(22) PCT Filed: Dec. 9, 2013

(86) PCT No.: PCT/EP2013/075954
§ 371 (c)(1),
(2) Date: Aug. 18, 2015

(87) PCT Pub. No.: WO2014/090748
PCT Pub. Date: Jun. 19, 2014

(65) Prior Publication Data
US 2015/0338212 A1    Nov. 26, 2015

(30) Foreign Application Priority Data

Dec. 11, 2012    (FR) .................................... 12 61870

(51) Int. Cl.
*G01B 11/30*    (2006.01)
*G01N 21/17*    (2006.01)

(52) U.S. Cl.
CPC .......... *G01B 11/303* (2013.01); *G01N 21/1717* (2013.01); *G01N 2021/1725* (2013.01); *G01N 2201/065* (2013.01)

(58) Field of Classification Search
CPC . G01N 2201/065; G01N 21/47; G01N 21/55; G01N 21/9503; G01N 21/8806; G01B 11/303; G01B 11/306; H01L 22/24
USPC ......... 356/326, 445–448, 600, 236, 432, 417; 250/228
See application file for complete search history.

(56) References Cited

U.S. PATENT DOCUMENTS 4,360,275 A    11/1982    Louderback
4,710,030 A *  12/1987    Tauc .................. G01N 21/1702
                                                            356/432

(Continued)

OTHER PUBLICATIONS

Plaza, J., et al., "Photoluminescence-free photoreflectance spectra using dual frequency modulation," Journal of Applied Physics 102, 093507 (2007), 5 pages.

(Continued)

*Primary Examiner* — Hoa Pham
(74) *Attorney, Agent, or Firm* — Pillsbury Winthrop Shaw Pittman LLP

(57) ABSTRACT

A photoreflectance device for characterizing a rough surface includes a pump beam emitter to emit a pump beam; a probe beam emitter to emit a probe beam; a detector to detect the probe beam reflected by the surface; an integrating sphere to collect the probe beam reflected by the surface, the integrating sphere including: a first output connected to the detector, and disposed so as to receive a majority of the probe beam reflected by the surface; a second output arranged so as to receive a majority of the pump beam reflected by the surface.

8 Claims, 1 Drawing Sheet

(56) References Cited

U.S. PATENT DOCUMENTS

| | | | |
|---|---|---|---|
| 5,159,410 | A | 10/1992 | Pollak et al. |
| 5,172,191 | A | 12/1992 | Dutta et al. |
| 5,255,070 | A | 10/1993 | Pollak et al. |
| 5,255,071 | A | 10/1993 | Pollak et al. |
| 5,270,797 | A | 12/1993 | Pollak et al. |
| 5,365,334 | A | 11/1994 | Bottka |
| 5,982,499 | A | 11/1999 | Chichester et al. |
| 6,195,166 | B1 | 2/2001 | Gray et al. |
| 7,239,392 | B2 | 7/2007 | Chism, II |
| 7,420,684 | B2 * | 9/2008 | Takeuchi ............ G01N 21/1717 356/432 |
| 7,755,752 | B1 | 7/2010 | Salnik et al. |
| 2002/0151127 | A1 * | 10/2002 | Liu ....................... B24B 37/042 438/200 |
| 2010/0284014 | A1 | 11/2010 | Baba et al. |

OTHER PUBLICATIONS

Ghosh, S., et al., "Photoreflectance spectroscopy with white light pump beam," Review of Scientific Instruments, vol. 69, No. 3, (1998), pp. 1261-1266.

Lu, C.R., et al., "Photoreflectance Study of the Internal Electric Fields at the n-Type GaAs Surface and Across the n-Type GaAs/Substrate Interface," Superlattices and Microstructures, vol. 8, No. 2, 1990, pp. 155-157.

International Preliminary Report on Patentability and the Written Opinion of the International Searching Authority as issued in International Patent Application No. PCT/EP2013/075954, dated Jun. 16, 2015.

* cited by examiner

PHOTOREFLECTANCE DEVICE

CROSS-REFERENCE TO RELATED APPLICATIONS

This is the U.S. National Stage of PCT/EP2013/075954, filed Dec. 9, 2013, which in turn claims priority to French Patent Application No. 1261870, filed Dec. 11, 2012, the entire contents of all applications are incorporated herein by reference in their entireties.

TECHNICAL FIELD

The present invention relates to a photoreflectance device for characterizing a rough or diffusing surface.

STATE OF PRIOR ART

Photoreflectance is a non-destructive process enabling a contactless probing in particular of semiconductor samples. Photoreflectance devices from prior art generally use a monochromatic probe beam to measure the light intensity reflected at the surface of a sample by means of a photodetector. A second beam, called a pump beam, which is a laser beam having a photon energy higher than the gap width of the sample, is also used to irradiate the surface of the sample so as to generate an electron/hole pair, which modifies the dielectric properties of the sample in the vicinity of its surface, and consequently the reflectivity of the sample for some wavelengths. The variation in light intensity from the probe beam reflected by the surface of the sample is measured, most often using synchronous detecting means. Thereby, a photoreflectance spectrum which is defined as the relative change in the reflection of the probe beam on the sample induced by the pump beam can be drawn. This photoreflectance spectrum is measured on a wide spectrum range, which enables semiconductor materials, semiconductor heterostructures, or even semiconductor interfaces to be characterised.

Such photoreflectance devices are for example described in documents U.S. Pat. No. 5,255,070, U.S. Pat. No. 5,255,071, U.S. Pat. No. 5,270,797, U.S. Pat. No. 5,159,410, U.S. Pat. No. 5,172,191, U.S. Pat. No. 5,365,334, U.S. Pat. No. 7,755,752, U.S. Pat. No. 6,195,166, U.S. Pat. No. 5,982,499, U.S. Pat. No. 7,239,392.

When the surface intended to be characterised is planar, the collimation and focusing of the reflected probe beam are not critical because most of the reflected light detected corresponds to the reflected probe beam. Consequently, the reflected probe luminous flux is high and can thus be easily detected. In the same way, the reflection of the pump beam is specular and is thereby not detected, which enables not to interfere with the measurement of the reflected probe beam. Indeed, the pump beam is only used to locally modify the dielectric properties of the material and it must not be detected in any case.

On the other hand, when the surface intended to be characterised is rough, a significant part of the probe beam is diffused rather than being reflected, and consequently, the intensity of the reflected probe beam is low. The reflected signal detected is thus low and the signal-to-noise ratio is very poor. Further, the pump beam is in turn diffused and consequently, part of the pump beam diffused is sensed by the detecting means, which interferes with the measurement of the reflected probe signal.

DISCLOSURE OF THE INVENTION

The invention aims at solving the drawbacks of the state of the art by providing a photoreflectance device which enables the signal-to-noise ratio to be maximized for a photoreflectance measurement, including when the probed surface has a high roughness.

For this, a first aspect of the invention provides a photoreflectance device for characterising a rough surface including:
  probe beam emitting means called "probe emitting means";
  pump beam emitting means called "pump emitting means";
  detecting means capable of detecting a beam reflected by the surface;
  an integrating sphere that can be disposed so as to collect the probe beam reflected by the surface, the integrating sphere including:
    a first output to which the detection means are connected, the first output being disposed so as to receive a majority of the probe beam reflected by the surface;
    a second output arranged so as to receive a majority of the pump beam reflected by the surface.

The integrating sphere enables the light quantity from the probe beam which is sensed by the detecting means to be increased. Indeed, the integrating sphere enables light from the probe beam diffused by the roughnesses to be collected in order to transmit it to the detecting means. Further, the second output enables the pump beam to be discharged from the integrating sphere in order not to transmit it to the detecting means.

Advantageously, the photoreflectance device further includes a high-pass filter provided between the first output of the integrating sphere and the detecting means. This high-pass filter enables the pump beam to be filtered in order not to transmit it to the detecting means.

According to preferential embodiment, the photoreflectance device further comprises first modulating means capable of modulating the probe beam at a frequency different from that of the pump beam. Modulating the probe beam at a frequency different from that of the pump beam enables to recover only the signal useful for characterising the surface.

Advantageously, the photoreflectance device further includes second modulating means capable of frequency modulating the pump beam. Modulating both the pump beam and the probe beam enables luminance and Rayleigh diffusion and direct diffusion components of the pump beam (laser) to be removed.

Preferably, the photoreflectance device further includes amplifying means capable of amplifying a signal received by the detecting means, which enables to have a more readily exploitable signal.

Preferably, the integrating sphere is positioned away from the sample so as not to damage it. The device thus enables to carry out contactless measurements.

Besides, the integrating sphere can preferably be moved in parallel to the surface of the sample so as to probe the entire surface of the sample.

The integrating sphere is moved with the focusing point of the probe and pump beams.

The probe emitting means preferably include a tunable polychromatic or monochromatic light source.

The pump emitting means preferably include a laser emitting photons the energy of which can be adjusted as a function of the band gap of the semiconductor or the energy gap of the semiconductor.

According to different embodiments:
  the detecting means can be directly connected to the first output of the integrating sphere, which enables signal losses to be restricted or even the detecting means can be connected to the first output of the integrating sphere via un optical fibre, which enables the integrating sphere to be more easily moved at the surface of the sample to be probed, since the detecting means are then not necessarily integral with the detecting sphere, and consequently, they do not have to be moved simultaneously to the integrating sphere.

BRIEF DESCRIPTION OF THE FIGURES

Further characteristics and advantages of the invention will appear upon reading the detailed description that follows, with reference to the appended figures, which illustrate.

For the sake of clarity, identical or similar elements are referred to with identical reference signs throughout the figures.

DETAILED DESCRIPTION OF AT LEAST ONE EMBODIMENT

Figure 1:
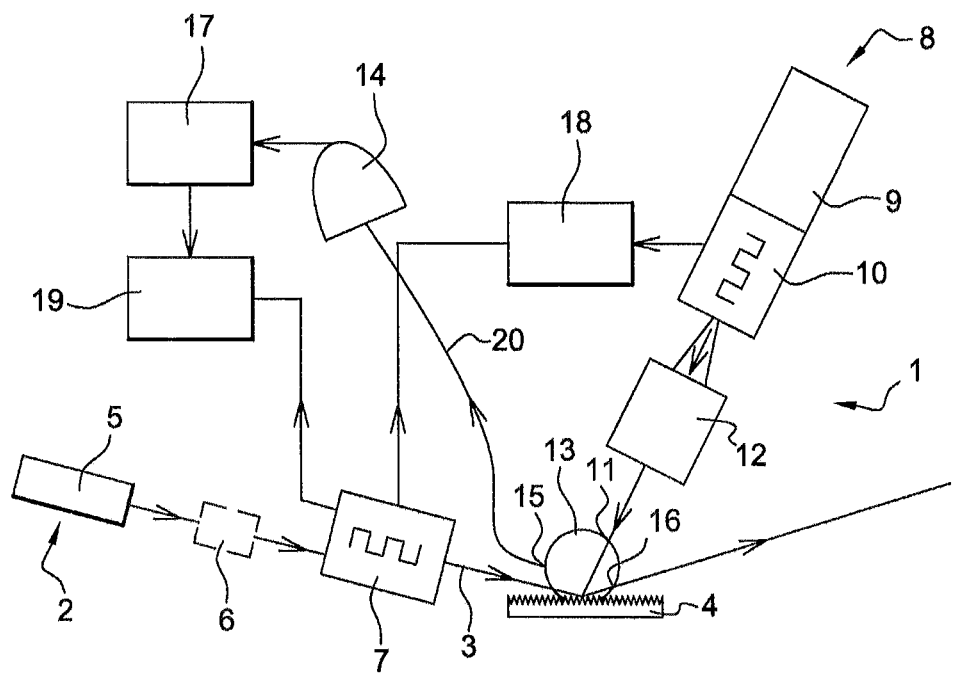
FIG. 1, a photoreflectance device according to one embodiment of the invention.

FIG. 1 represents a photoreflectance device according to one embodiment of the invention enabling the surface 4 of a sample to be characterised. This photoreflectance device 1 includes pump emitting means 2 capable of emitting a pump beam 3. This pump beam 3 is reflected by the sample. The pump emitting means 2 of the pump beam preferably include:
- a laser 5 emitting photons the energy of which can be adjusted as a function of the gap energy of the material to be characterised:
- a variable density neutral grey filter 6 enabling the pump light flux to be adjusted to the sample. Alternatively, instead of using this neutral variable density filter 6, the power can also be adjusted to the pump laser supply;
- second modulating means 7 capable of modulating the pump beam in frequency.

The photoreflectance device further includes probe emitting means 8 capable of emitting a probe beam 11. These probe emitting means 8 preferably include:
- a tunable polychromatic or monochromatic light source 9;
- first modulating means 10 capable of modulating the probe beam in frequency;
- collimating means 12 capable of making and keeping parallel the rays of the probe beam 11.

The photoreflectance device also includes an integrating sphere 13 which enables the probe beam which is reflected and diffused by the surface of the sample to be collected. The integrating sphere preferably has a diameter between 800 and 1200 mm.

The photoreflectance device also includes detecting means 14 which enable the probe beam 11 reflected by the surface of the sample to be detected. The detecting means 14 preferably include a synchronous light detector.

The integrating sphere includes:
- a first output 15 to which the detecting means 14 are connected, the first output being disposed so as to receive a majority of the probe beam 11 reflected by the rough surface;
- a second output 16 arranged so as to receive the specular beam of the pump beam 3 reflected by the rough surface.

Figure 2:
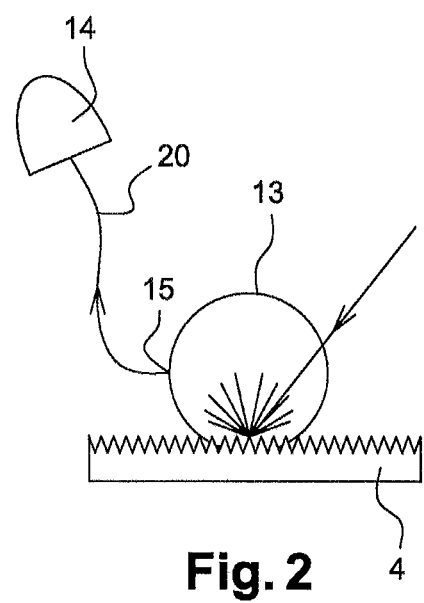
FIG. 2, the integrating sphere and the detecting means of the device of FIG. 1.
Figure 3:
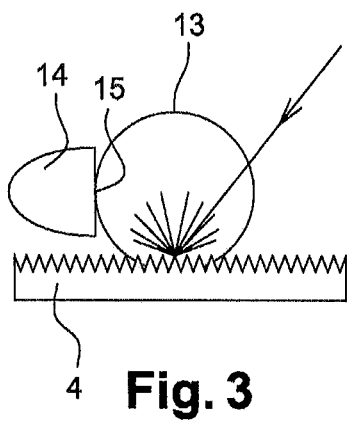
FIG. 3, an alternative embodiment of FIG. 3.

As represented in FIG. 3, the first output 15 can be directly connected to the detecting means 14, or as represented in FIGS. 1 and 2 via an optical fibre 20.

The photoreflectance device also includes amplifying means 17 connected to the detecting means and enabling the signal received by the detecting means to be amplified.

The photoreflectance device also includes first synchronous detecting means 18 enabling the signal to be efficiently extracted.

The photoreflectance device also includes second synchronous detecting means 19 enabling the signal to be efficiently extracted.

The operation of the photoreflectance device will now be detailed.

The probe beam 11 and the pump beam 3 are focused at the same place of the sample, that is at the place of the surface of the sample intended to be characterised. The pump beam 3 irradiates the surface 4 of the sample, which creates a photovoltaic effect in the vicinity of the surface of the sample through the generation of electron/hole pairs, thus locally modifying the dielectric properties. The probe beam 11 is reflected by the surface of the sample. The reflection of the probe beam 11 is modified by the pump beam. The photoreflected spectrum is defined as the relative change in the reflection of the probe beam induced by the pump beam.

The integrating sphere 13 enables the intensity of the probe beam which is reflected and diffused by the surface of the sample to be collected. The second output 16 of the integrating sphere enables the specular reflection of the pump beam reflected by the sample to be left out so as not to transmit it to the detecting means.

Further, modulating the probe beam by the first modulating means enables to transmit to the detecting means only the intensity from the probe beam, without transmitting parts of the pump beam. This dual frequency modulation principle has been used for the first time by Lu. C R et al. 1990, "Photoreflectance study of the internal electric fields at the n-type GaAs surface and across the n-type GaAs/substrate interface", Superlattices and microstructures, 8(2), pp. 155-157. A more detailed explanation is provided by Plaza et al. (2007), Photoluminescence-free photoreflectance spectra using dual frequency modulation, Journal of Applied Physics, 102(9), 093507, and Ghosh et al. Ghosh (1998), Photoreflectance spectroscopy with white light pump beam, Review of Scientific Instruments, 69(3), 1261.

Further, the dual modulation of the pump beam and probe beam enables luminescence and Rayleigh diffusion and direct diffusion components of the pump beam to be removed.

The device according to the invention can in particular be used to perform non-destructive monitorings for the photovoltaic industry.

Naturally, the invention is not limited to the embodiments described with reference to the figures and alternatives can be contemplated without departing from the scope of the invention. A multichannel detector can especially be used as a detecting means, which enables the acquisition of a signal with several wavelengths to be simultaneously carried out.

The invention claimed is:

1. A photoreflectance device for characterising a rough surface, comprising:
    a pump beam emitter configured to emit a pump beam;
    a probe beam emitter configured to emit a probe beam;
    a detector configured to detect a beam reflected by the surface, and
    an integrating sphere that is disposed so as to collect the probe beam reflected by the surface, the integrating sphere including:
        a first output to which the detector is connected, the first output being disposed so as to receive a majority of the probe beam reflected by the surface;

a second output arranged so as to receive a specular reflection from the pump beam reflected by the surface.

2. The photoreflectance device according to claim 1, further comprising a first beam modulator configured to modulate the probe beam at a frequency different from that of the pump beam.

3. The photoreflectance device according to claim 1, further comprising a second beam modulator configured to modulate the pump beam in frequency.

4. The photoreflectance device according to claim 1, further comprising a signal amplifier configured to amplify a signal received by the detector.

5. The photoreflectance device according to claim 1, wherein the probe beam emitter of the probe beam includes a monochromatic light source.

6. The photoreflectance device according to claim 1, wherein the pump beam emitter of the pump beam includes a laser to emit photons the energy of which is adjustable as a function of a gap energy of a material to be characterised.

7. The photoreflectance device according to claim 1, wherein the detector is directly connected to the first output of the integrating sphere.

8. The photoreflectance device according to claim 1, wherein the are detector is connected to the first output of the integrating sphere via an optical fibre.

\* \* \* \* \*